United States Patent [19]

Cornwell

[11] Patent Number: 4,457,299
[45] Date of Patent: Jul. 3, 1984

[54] INCONTINENCE CONTROL DEVICES

[76] Inventor: George H. I. Cornwell, 21 Talbot Rd., Harrow Weald, Middlesex, England

[21] Appl. No.: 263,147

[22] Filed: May 13, 1981

[30] Foreign Application Priority Data

Feb. 6, 1981 [GB] United Kingdom ................. 8103675

[51] Int. Cl.³ ............................................. A61B 19/00
[52] U.S. Cl. ............................ 128/1 R; 128/DIG. 25
[58] Field of Search .......... 128/1 R, DIG. 25, 138 R, 128/132

[56] References Cited

U.S. PATENT DOCUMENTS

| 3,463,141 | 8/1969 | Mozolf | 128/1 R |
| 3,768,102 | 10/1973 | Kwan-Gett | 128/1 R |
| 3,797,478 | 3/1974 | Walsh et al. | 128/DIG. 25 |
| 3,958,556 | 5/1976 | Schenk | 604/48 |
| 4,209,009 | 6/1980 | Hennig | 128/DIG. 25 |

FOREIGN PATENT DOCUMENTS

| 504554 | 8/1930 | Fed. Rep. of Germany | 604/349 |
| 2810973 | 11/1978 | Fed. Rep. of Germany | 128/1 R |

Primary Examiner—C. Fred Rosenbaum
Assistant Examiner—J. L. Kruter
Attorney, Agent, or Firm—Kemon & Estabrook

[57] ABSTRACT

This invention relates to internally prestressed flexible capsule devices for insertion within or partly within the male and female urethra for the specific purpose of the automatic and/or manual control of urinary incontinence which is effected by a prestressed device deforming the lower interior of the urethra into a broadly elliptical shape stressed slightly in excess of the involuntary pressure, and such that the devices deform or collapse on their cross-section at the increased urine voiding pressure and open a free urine bypass cross-section area and when voiding ceases the capsule device returns to its maximum cross-sectional area for involuntary urine flow control ready for repeat cycles as selected.

5 Claims, 16 Drawing Figures

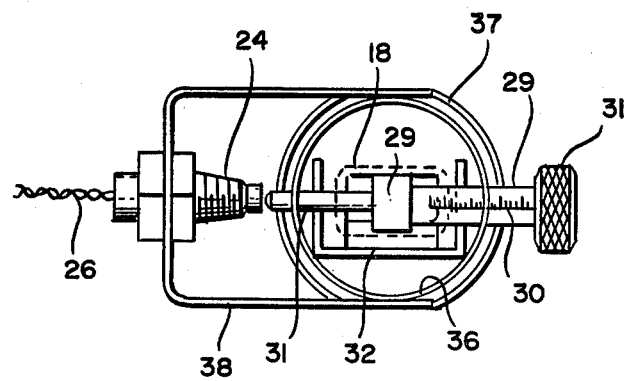
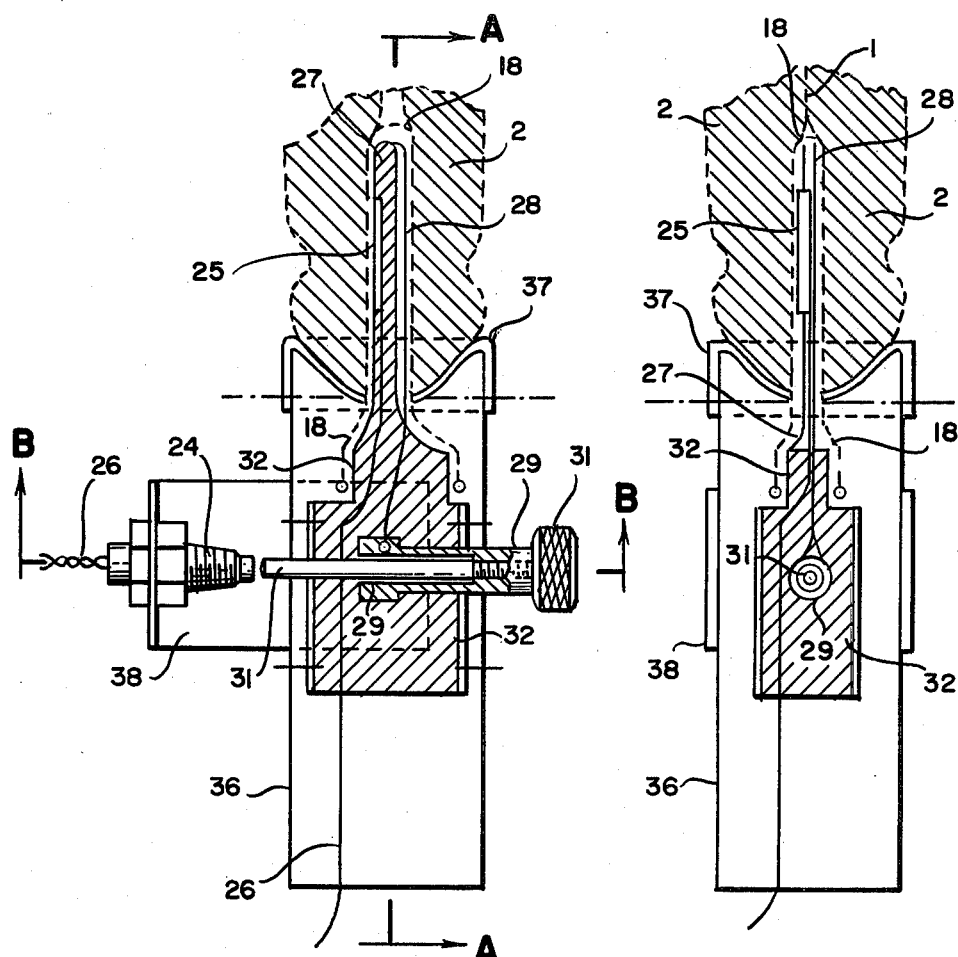
Fig. 9
Fig. 10
Fig. 11

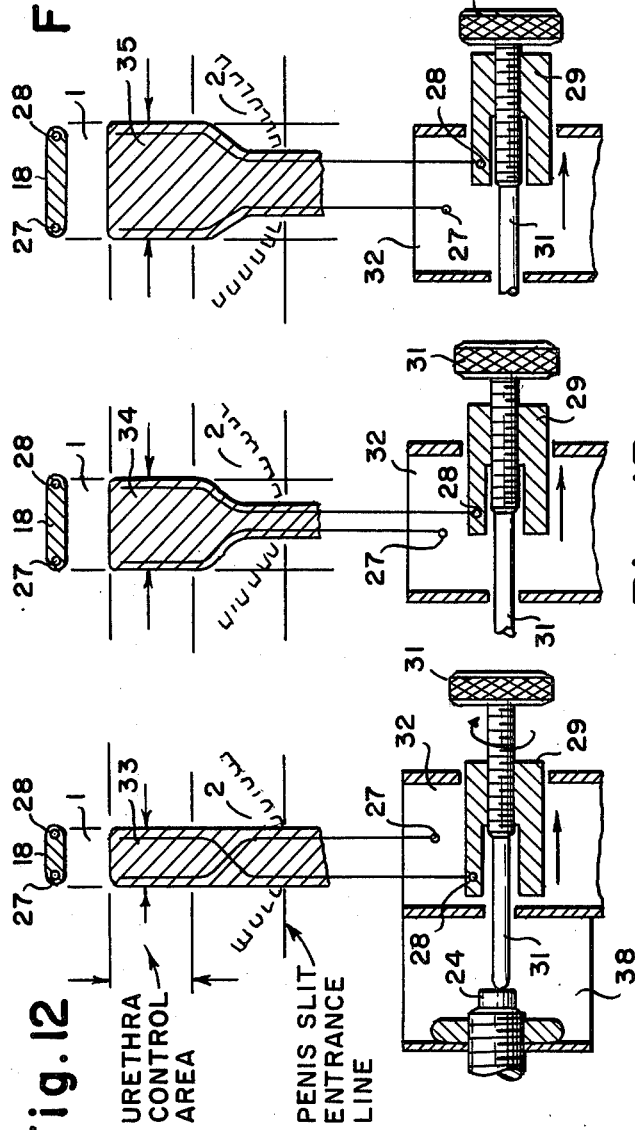

4,457,299

INCONTINENCE CONTROL DEVICES

This invention relates to devices for controlling or mitigating the urinary incontinence of human male or female persons and which are hereinafter referred to as urinary control devices (UCD).

BACKGROUND OF THE INVENTION

According to written medical statistics ten percent of the human population (400 million) suffer from temporary or permanent urinary incontinence or the inability of the human body sphincter muscles to control urination to appropriate selected times and place.

The human bladder as soon as any urine is collected within allows it to flow away past the faulty sphincter muscles to the external urethra exit where it causes considerable inconvenience.

Existing devices consist of the external attachment of large and obvious devices such as drainage bags, penis constriction straps, soaking pads, etc.

These with the exception of the penis constriction strap, are only external collectors or absorbers of urine without any form of involuntary urine flow control.

The external penis control device does control involuntary urination, and is externally released when urination is required.

It is towards the solution of this problem in a better and more inconspicuous way that this invention is directed.

SUMMARY OF THE INVENTION

The involuntary urine flow control device is a completely sealed flexible internally prestressed unit and selected for size and pressure prior to insertion into its urethra urine control situ where to prevent involuntary urination it exerts a direct pressure upon the urethra internal wall slightly in excess of the involuntary voiding pressure and is in its preferred embodiment of a broadly elliptical or oval form, and such that with the physical pressure increase for selected urination or voiding the device is deformed or collapsed upon its cross-section within the now circular cross-section urethra leaving an adequate urethra unoccupied cross-section area open for the urine to void between the control device and the urethra wall.

To enable the correct urine flow control device to be selected for a particular urethra diameter size and pressure special tools have been designed for pretesting each urethra before selection and insertion of the control device and as are specified herein.

DESCRIPTION OF THE DRAWINGS

FIG. 9 is as FIG. 7 but with the sealed device (7) hollow (14) and filled with a liquid or gas (15) under prestressed pressure;

FIG. 10 shows a cross-section of FIG. 9 with the urethra voiding urine and the device (7) compressed and deformed under the voiding urine pressure;

FIG. 11 shows a cross-section of FIGS. 5 and 6 with the control device in close contact with the urethra wall (1) and a non-voiding urine area between same, the said device comprising a sealed external flexible prestressed envelope sheath (12) within which is located a prestressed loop spring (10) and filled with prestressed fluid or gas (15) under pressure;

FIG. 12 as FIG. 11 with the voiding urethra showing a deformed control device (12);

FIG. 13 shows as FIG. 12 the same device compressed (within the circular urine voiding urethra area) to a different cross-sectional shape (12);

FIG. 14 shows as FIG. 11 a urine control device (12) but with a second internal prestressed flat spring (17) formed into a contour to lay parallel and in contact with the internal flexible sheath wall of the device (12) the purpose being that when the device is flexed by voiding urine pressure, the device will always under compression be deformed in one way only as shown in FIG. 15;

FIG. 15 shows as FIG. 8 the device of FIG. 14 under voiding urine compression in a similar manner as explained in FIGS. 8, 10 and 12;

FIG. 16 shows a solid urine flow control device (7) in its non-voiding shape within the urethra (1) and in close contact with the urethra wall;

FIG. 17 shows as FIG. 16 the same device compressed within the circular urethra in a urine pressure voiding form;

FIG. 18 shows a vertical section through a male penis (2) with a urine control device (19) and withdrawal loop (3 and 4) located within the urethra and integrally attached to a prostate gland area (22) urethra fixed distending device (21) with its urine control device in a non-urinating situation;

FIG. 19 shows the same device as FIG. 18 but with a horizontal section showing the plan view of the control device (19) within the urethra (1);

FIG. 20 shows a cross-section and elevation of a mechanical transducer urethra pressure and sizing device;

FIG. 21 shows a cross-section plan of the same device as FIG. 20 with the sizing probes and transducer located within the urethra ready for test purposes;

FIG. 22 shows a cross-section side elevation of the urethra sizing device as shown in FIGS. 20 and 21;

FIG. 23 shows a diagrammatic plan of the operation and measuring principle of the urethra sizing tool probes without the transducer. This Figure shows the probes (27 and 28) relative positions as inserted in their smallest cross-section size (33);

FIG. 24 shows as FIG. 23 the same sizing test probes, in a middle distended cross-section size (34);

FIG. 25 shows as FIG. 23 the same sizing test probes, in their maximum distended cross-section size (35);

FIG. 26 shows a cross-section of the urethra sizing tool probes (27 and 28) and the calculation dimension symbols; and FIG. 27 shows a cross-section through an alternative urethra pressure and sizing test tool probe comprising an inflatable flexible balloon (39) with a transducer (25) attached to its exterior parallel with its longitudinal axis and with both the transducer (25) and the inflatable pressure balloon (39) exterior walls in close pressure contact with the urethra wall interior (1).

Figure 1:
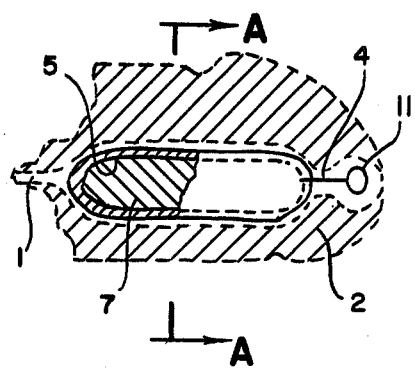
FIG. 1 shows a plan view of the urine prestressed control device (7) in situ within a non-voiding urethra (1) with external serrations (6)

In the various figures of the accompanying drawings the references used indicate components which are as follows:

1. Urethra or urethra wall-non-voiding urine.
2. Penis body.
3. External anti-migratory withdrawal loop.
3. Anti-migratory link connecting (3) to UCD capsule.
5. Internal UCD strengthening cords or prestressed metal or plastic loop.
6. UCD-urethra surface contact striations, indentations or matt exterior.
7. UCD-flexible body, solid or porous gel, rubber or plastic.
8. Urethra wall-inflated voiding urine.
9. UCD-urethra edge contact serrations.
10. Spring-prestressed metal or plastic.
11. UCD-internal located withdrawal and anti-migratory loop.
12. Outer sealed flexible rubber or plastic sheath.
13. Urethra urine-flow cavity or voiding area.
14. Internal cavity-vacuum, gas or liquid.
15. UCD-air, gas or liquid interior.
16. Urine flow direction: relative to FIGS. 1 to 6.
17. Single side-internal prestressed plastic or metal spring.
18. Urethra-rubber probe sheath.
19. Typical prestressed loop-UCD capsule.
20. Flexible link cord between UCD and (21).
21. Perforated prostate-urine flow tube.
22. Enlarged prostate gland area.
23. Scrotum.
24. External transducer or pressure guage.
25. Urethra internal pressure transducer.
26. Pressure transducer leads.
27. Fixed probe urethra sizing tool.
28. Adjustable probe urethra sizing tool.
29. Adjustable probe-movable anchor urethra sizing tool.
30. Urethra width measuring scale.
31. Adjustable probe movement and pressure screw.
32. Internal fixed probe anchor.
33. 5 mm. width-probe insertion test assembly.
34. 12 mm. width probe insertion test assembly.
35. 15 mm. width probe insertion test assembly.
36. Tube handle.
37. Penis flexible pressure pad.
38. External pressure guage or transducer support.
39. Test balloon-pressure flexible rubber.

DESCRIPTION OF A PREFERRED EMBODIMENT

A typical preferred type of urinary control device is as shown in FIGS. 6, 11, 12 and 13 and comprises an air tight and liquid-proof inflatable and flexible silicone rubber sheath (12) which may be impregnated on its exterior with antibiotics within which is located a suitably shaped loop (10) of prestressed plastic or metal, one end of which emerges from a sealed sheath exit with a semi-rigid link cord (4) on which may be formed either an internal anti-migratory loop (11) and/or an external anti-migratory, insertion and removal loop cap (3) with an orifice in same to permit the unobstructed flow of urine when voiding.

The UCD sheath before sealing would be pressure filled preferably with a gas (15) but it could be a liquid (15) at the specified pressure and then sealed.

After manufacture the external major cross-section periphery dimension would be test sized at the specified pressure to be applied for involuntary urine control within the urethra.

This data would be recorded, and enclosed with each UCD manufactured before enclosing and sealing within the sterile safe transit pack before despatch to the customer.

Figure 6:
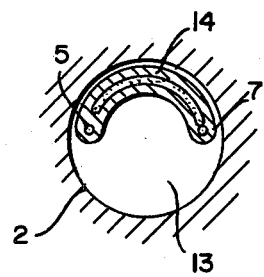
FIG. 6 as FIG. 5 but incorporating an integral insertion and withdrawal loop (3) and (4)

FIG. 6 shows a plan view of the preferred embodiment within a non-voiding urethra (11), and the UCD in its maximum cross-section urine control shape.

FIG. 11 shows a cross-section of the UCD also in its non-voiding urine control shape.

FIG. 12 and FIG. 13 show two possible variations of the UCD compressed on its cross-section within a voiding urine fully inflated urethra, with the free urine flow-urethra cross-section (13).

This same UCD is also shown in situ within a male penis in FIGS. 18 and 19 in which are shown additional attachments-flexible link cord (20) connected to a perforated semi-flexible prostate tube (21).

This latter (21) being inserted into the area (22) affected by an enlarged prostate gland to open the urethra tube interior sufficiently to eliminate urine flow restriction at this point when urine voiding is required.

This same form of UCD as FIG. 6 with external attachment cords may also be located within a female urethra where it will operate in a similar manner to that of a male urethra.

This device is also shown with various other additions and materials in FIGS. 1 to 19.

Internal UCD prestressing implies that the control devices and their materials are designed to be under predetermined external compression stresses when located in situ within the urethra, and are related to both the involuntary and voiding urine pressures involved such that at the involuntary voiding pressures the device remains in its designed static cross-sectional non-voiding area shape, and is compressed at the voluntary voiding pressure to a different reduced cross-sectional area and shape which will open an adequate cross-sectional area between the urethra internal wall and the control device exterior to permit the selected urination period and situation.

When controlled voiding ceases and the physical voiding pressure reduces to the involuntary voiding pressure the device returns to its static normal involuntary urine control flow, shape and position.

All typical and preferred devices show the basic operation principles but may be modified as necessary to improve or vary their efficiency or performance.

All control devices have incorporated suitably sized, shaped, pressurized and/or pre-pressurized components to accommodate any encountered size or shape of urethra and involuntary or voluntary pressure generated therein by any human or large animal patient or recipient.

For various typical and some preferred types of UCD devices refer to descriptions in the lists of section diagrams and component units.

Urethra pressure and sizing test fixture: FIGS. 20, 21 and 22 show a mechanical urethra sizing and pressure testing tool required to individually size and pressure test every deflated non-urine voiding urethra to which an individual prestressed UCD is to be fitted prior to the selection of an appropriate UCD.

The device has a probe arrangement comprising fixed probe (27) attached to anchor plate (32) which in turn is rigidly fixed to and within the main body handle (36) also parallel to (27) within the probe assembly is an adjustable probe (28) which in turn is rigidly attached to the movable anchor (29) having engraved upon its exterior a sizing scale (30).

Within the anchor (29) is an adjustable screw (31) which when rotated moves the anchor (29) and probe (28) axially and at right angles to the axis of probe (27) by means of the incorporated related meshing threads upon (29) and (31).

Enclosing both probes (27) and (28) for sterility is attached a flexible rubber sheath (18) which is retained in position by its reinforced elastic opening being pushed over a suitable location on the anchor plate (32).

The urethra probe in use is inserted within the urethra to a selected depth determined and controlled by the penis location pressure pad (37).

In preparation for insertion of the test probe the rubber sheath is lubricated with an antibacterial gel, and prior to insertion the adjustable movable sizing and pressure screw (31) is rotated anti-clockwise so that the width at right angles to the probe axis is at a minimum, usually 5 mm. (33) see FIG. 23 which shows the penis entrance size formed in such a manner as to reduce expansion of the penis slit entrance to a minimum during the test probe insertion and sizing operation.

When inserted and sizing is taking place the adjustment screw (31) is rotated clockwise in the opposite direction to increase the width at right angles to the probe axis which may be increased to as much as 17 mm. (35) depending upon the patient (see FIGS. 24 and 25).

FIG. 26 shows a diagrammatic section through the probe assembly head.

When the probes are nearly fully adjusted within the urethra pressure will be exerted by the urethra upon the external sides of the two probes (27) and (28) FIG. 21 and (27) and (28) FIG. 26 which will increase as the probe gap (33, 34 and 35) is progressively increased.

This pressure will be indicated by a pressure gauge located at (24) due to the applied tip pressure of the adjustable pressure screw (31) alternatively a pressure transducer (24) located firmly on a support (38) which in turn is secured to the handle (36) and/or an internal pressure transducer (25) located internally or externally to the flexible probe sheath (18) to read out upon a digital control indicator, via leads (26).

When the urethra wall in contact with sheath (18) applies the desired pressure upon the sides of the two probes (27) and (28) and transducers (24 and 25) adjustment of screw (31) is stopped and the urethra dimension read out upon scale (30) which relates to dimension W on FIG. 26.

The results should be recorded and then the adjustable screw 31 rotated anti-clockwise so as to relax the probe pressure and return same to the minimum position (33) FIG. 23 to allow easy removal of the probe assembly and pressure tool complete from the urethra.

The permissable and required prestressed pressure within the uretha comprises, the summation of several component pressures as listed below all of which have to be considered.

The peripheral dimension of a section taken through the inserted assembly shown (FIG. 26) is: $\{2(W-d)+\pi d\}$ mm. and this will be equal to the required elliptical periphery of the maximum cross section taken through a prestressed and undeformed UCD to be inserted within that particular urethra for the control of involuntary urination at a pressure of $P_{CT}$.

For test purposes the dimension (d) should preferably be as small as possible (e.g. about 1 mm.).

From the known UCD elliptical periphery dimension obtained as shown above a UCD may be selected with an equivalent maximum cross-sectional size and prestressed at the selected and required pressure.

The resultant pressure guage or transducer digital read-out pressure will comprise the following components:

$$P_{TP}=\{P_{LS}+(P_{CP}+P_E+P_M)\} \text{ OR}$$
$$P_{LS}=(P_{TP}-P_{CT})$$

where $P_{TP}$=Total pressure as shown on the digital read-out.

$P_E$=External atmospheric pressure being applied onto the relaxed flattened urethra tube.

$P_M$=Muscular residual pressure if any within the non-sphincter controlled urethra test area.

$P_{LS}$=Latex sheath stretch pressure and size required during mechanical sizing tests—previously measured with the mechanical device for different urethra widths on scale (30) prior to insertion within the urethra, and check tested for each different sheath being used on the test device.

$P_{CP}$=Control pressure—the selected additional pressure to be applied to the urethra interior by the UCD selected to control involuntary urination—dependent upon the patient and his requirements.

UCD Total control pressure within urethra=$P_{CT}=\{P_{CP}+(P_E+P_M)\}$

Note: The combined $(P_E+P_M)$ can be directly obtained by insertion of a pressure transducer probe into the urethra area being treated and recording the digital read out prior to the commencement of the sizing test.

The desired pressure in transducer (25) will be $(P_{CT})=(P_{CP}+P_E+P_M)$ and from the dimension (W) at this point and the preceding formulae the urethra circumference can be calculated directly.

Alternatively or as a check, the desired pressure on transducer or gauge (24) will be $(P_{TP})$ and with the known pressure of transducer (25) of $(P_{CT})=(P_{CP}+P_E+P_M)$. Value $(P_{LS})$ can be calculated from the preceding formula.

Thus for the control pressure $(P_{CT})$ and using $(P_{LS})$ in conjunction with the precalculated and supplied pressure and size tables the related urethra diameter and circumference dimensions will be given for the equivalent UCD.

These supplied Tables will have printed upon them for various $(P_{LS})$ pressures, the equivalent sheath diameter and hence urethra diameter and circumference, related specifically with the type and size of sizing test sheath being used for the test and its equivalent UCD dimension.

The preferred sizing and pressure test fixture for the urethra is described as follows:

FIG. 27 shows an alternative method (based upon the previous formulae) of measuring the urethra internal diameter (1) at any preselected internal control pressure ($P_{CT}$) which may be effected by inserting into the urethra (1) an inflatable sizing test balloon (39) externally connected to a pressurizing bladder and a transducer digital read-out.

Also at the same time a second transducer (25) is inserted into the urethra between the urethra wall (1) and the adjacent outer wall of the test balloon (39).

For testing the balloon (39) would be inflated until the second transducer (25) reads out the UCD combined pressure of $$(P_{CT}) = \{P_{CP} + (P_E + P_M)\}$$

At this point the first transducer will read out the pressure within the inflatable test balloon ($P_{TP}$) (39).

From the above data as explained previously ($P_{LS}$) can be easily calculated as for transducers (24) and (25) on the previous test fixture, and the corresponding sheath or urethra diameter and circumference related to the specific test balloon (39) used in the test and the correlated UCD dimension.

In this type of test tool after the test has been done and the pressure ($P_{LS}$) obtained, the test probe is deflated and withdrawn.

The test probe balloon (39) may now externally to the urethra be reinflated to pressure ($P_{LS}$) and its outside diameter can be measured with a micrometer, or inserted into one of a set of supplied ring or gap gauges.

Hence the circumference at ($P_{LS}$) can be calculated and related to the UCD required and its equivalent corresponding major axis cross-sectional periphery at the control pressure ($P_{CT}$).

This test device has the added advantage that the tool supplier does not have to test and supply size and pressure tables for each test probe bladder made.

The ($P_{LS}$) and dimension being always obtained at the time of the test by the urologist, and it is also not dependent upon the ambient test area temperature at the time of the test.

It may well be decided on the early stages of the use of UCD's until sufficient field data is obtained that every six months or as required each patient will be retested as the urethra size may expand slightly either due to the increasing age of the user or the application of the UCD.

All urethras have to be individually sized and pressure tested by the urologist prior to the fitting of a UCD as urethra sizes may vary from 5.5 mm to 10 mm inside diameter when inflated (i.e., urine voiding). This has to be done by the urologist with a specially designed sizing and pressure testing tool and the data obtained recorded and related to the correct size of specified UCD.

For example, the test fixture probe is inserted within the urethra to the control area situ, and is inflated to ascertain the internal diameter of the urethra at the required involuntary urine control pressure, this is then related to the selection of the required UCD.

The forms of designed test tools are hereinafter described with the preferred type specified, also specified is the operating instructions and the data obtained therefrom.

I claim:

1. A urethra insertable urinary control device comprising a flexible completely sealed capsule means with an exterior sheath, said capsule means having a non-spherical cross-section to a longitudinal axis with a major sectional axis and a minor sectional axis, said capsule means being internally stressed by at least one prestressed spring, said spring being located in said capsule means to apply pressure axially along the major sectional axis of the capsule means whereby said capsule means with sheath when inserted in the urethra applies a predetermined calculated pressure along the internal wall of the urethra so as to distort the cross-sectional shape of the urethra by capsule means distortion to prevent involuntary urination, said prestressed spring having an integral and unitary extension means at one end thereof, said extension means projecting from the capsule means and having an integral insertion antimigratory spring and withdrawal device thereon, and said capsule means when subjected to an increase in physical voiding pressure deforming against the action of said spring along one side of its major sectional axis so as to open a free voiding area in the urethra for voluntary urination between the internal wall of the urethra and the external wall of the capsule means.

2. A device as claimed in claim 1, wherein the flexible internally prestressed capsule means is of a broadly elliptical cross-section of a predetermined pressure and size so as to stress the urethra internal wall at a pressure sufficient to eliminate involuntary urination.

3. A device as claimed in claim 2, wherein said control member comprises a solid capsule.

4. A device as claimed in claim 2, wherein the capsule means is in the form of a hollow sheath having a prestressed spring therein, and said sheath being filled with a liquid or gas under pressure.

5. A device according to claim 1, wherein the external surface of the control device is matt, serrated or striated so as to reduce capillary leakage when the capsule means is fitted within the urethra.

* * * * *

UNITED STATES PATENT AND TRADEMARK OFFICE
CERTIFICATE OF CORRECTION

PATENT NO. : 4,457,299

DATED : July 3, 1984

INVENTOR(S) : George H. I. Cornwell

It is certified that error appears in the above-identified patent and that said Letters Patent is hereby corrected as shown below:

Columns 1 through 8 inclusive should be deleted and the attached pages consisting of columns 1 through 8 substituted therefor.

Signed and Sealed this

Eighteenth Day of December 1984

[SEAL]

Attest:

GERALD J. MOSSINGHOFF

Attesting Officer

Commissioner of Patents and Trademarks

INCONTINENCE CONTROL DEVICES

This invention relates to devices for controlling or mitigating the urinary incontinence of human male or female persons and which are hereinafter referred to as urinary control devices (UCD).

BACKGROUND OF THE INVENTION

According to written medical statistics ten percent of the human population (400 million) suffer from temporary or permanent urinary incontinence or the inability of the human body sphincter muscles to control urination to appropriate selected times and place.

The human bladder as soon as any urine is collected within allows it to flow away past the faulty sphincter muscles to the external urethra exit where it causes considerable inconvenience.

Existing devices consist of the external attachment of large and obvious devices such as drainage bags, penis constriction straps, soaking pads, etc.

These with the exception of the penis constriction strap, are only external collectors or absorbers of urine without any form of involuntary urine flow control.

The external penis control device does control involuntary urination, and is externally released when urination is required.

It is towards the solution of this problem in a better and more inconspicuous way that this invention is directed.

SUMMARY OF THE INVENTION

The involuntary urine flow control device is a completely sealed flexible internally prestressed unit and selected for size and pressure prior to insertion into its urethra urine control situ where to prevent involuntary urination it exerts a direct pressure upon the urethra internal wall slightly in excess of the involuntary voiding pressure and is in its preferred embodiment of a broadly elliptical or oval form, and such that with the physical pressure increase for selected urination or voiding the device is deformed or collapsed upon its cross-section within the now circular cross-section urethra leaving an adequate urethra unoccupied cross-section area open for the urine to void between the control device and the urethra wall.

To enable the correct urine flow control device to be selected for a particular urethra diameter size and pressure special tools have been designed for pretesting each urethra before selection and insertion of the control device and as are specified herein.

Figure 2:
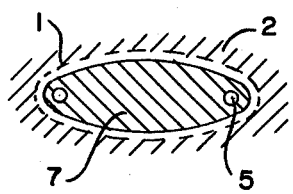
FIG. 2 as FIG. 1 without serrations and incorporating an internal prestressed spring loop or cord (5) attached to an anti-migratory loop (11)
Figure 3:
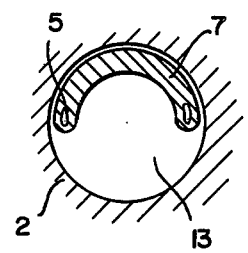
FIG. 3 as FIG. 2 but with the prestressed spring loop (10) protruding from both ends of the control device and with edge serrations (9)
Figure 4:
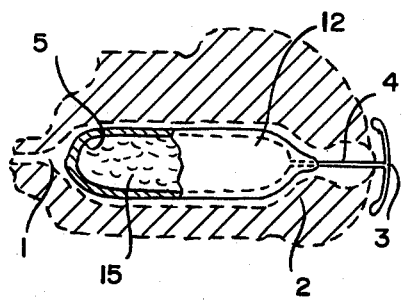
FIG. 4 as FIG. 3 but with both edges of the flexible body serrated (9)
Figure 5:
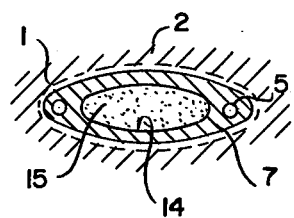
FIG. 5 shows a plan view of the prestressed urine control device in situ within a non-voiding urethra (1) comprising a sealed hollow flexible sheath (12), within which is incorporated a prestressed loop spring (10), anti-migratory loop (11), and a pressurized liquid or gas filling (15)
Figure 7:
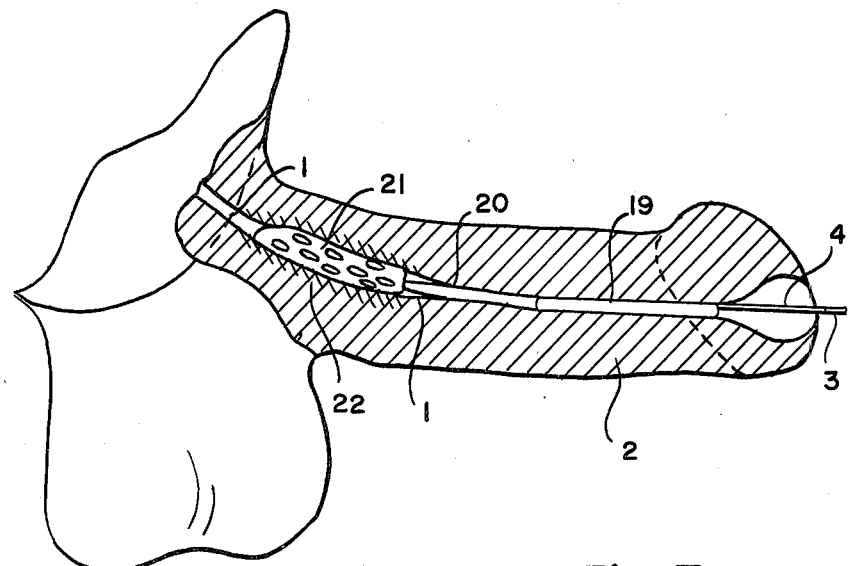
FIG. 7 shows a horizontal axis section of the control device as FIG. 2 in its involuntary urine flow control shape within the urethra (1) comprising a solid flexible body (7) within which is an internal spring (10)
Figure 8:
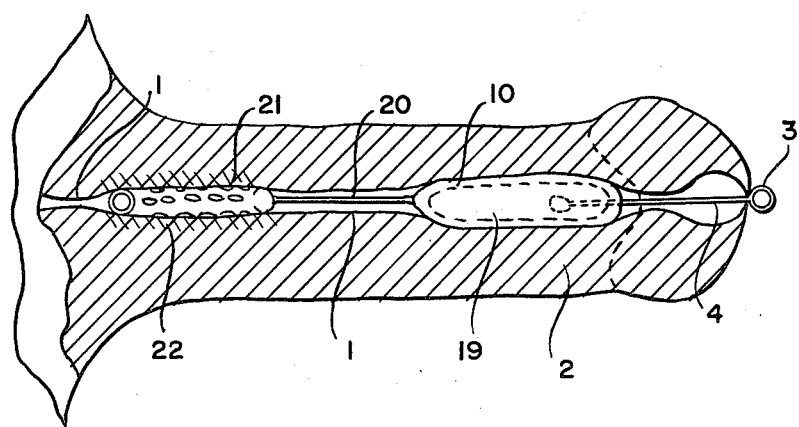
FIG. 8 shows a cross-section of FIG. 7 with the urethra (8) inflated, passing urine (13) via the inflated urethra and the compressed deformed control device (7), due to the increased urine voiding pressure.

The invention will now be described by way of example with reference to the accompanying drawings in which:

FIG. 1 is a diagrammatic sectional elevation through a preferred embodiment of a control device in accordance with the invention showing the control device in situ within the urethra of a male penis;

FIG. 2 is a section on the line A—A of FIG. 1 showing the control device in position in the urethra with its cross-sectional shape stressed to prevent involuntary urination;

FIG. 3 is a section similar to FIG. 2 but showing the urethra inflated with the control device compressed and distorted to allow voluntary urination due to the increased urine voiding pressure;

FIG. 4 is a diagrammatic sectional elevation through a modified embodiment of a control device similar to that of FIG. 3 but comprising a sealed hollow flexible sheath containing a pressurized liquid or gas filling in addition to the prestressed loop or spring of the FIG. 1 embodiment;

FIG. 5 is a sectional view similar to FIG. 2 but showing a modification of the FIG. 1 embodiment in which the capsule forming the control device is hollow and filled with a liquid or gas under pressure;

FIG. 6 is a sectional view similar to FIG. 3 and showing the FIG. 5 embodiment of the control device in its compressed and deformed condition under voiding urine pressure;

FIG. 7 shows a vertical section through a urine control device located within the urethra of a male penis and integrally attached to a urethra fixed distending device in the prostate gland area;

FIG. 8 shows the same device as FIG. 7 but with a horizontal section showing the plan view of the control device within the urethra;

FIG. 9 shows a cross-sectional elevation taken on line B—B of FIG. 10 of a mechanical transducer urethra pressure and sizing device;

FIG. 10 shows a cross-sectional plan of the same device as FIG. 9 with the sizing probes and transducer located within the urethra ready for test purposes;

FIG. 11 shows a cross-sectional side elevation of the urethra sizing device as shown in FIGS. 9 and 10;

FIG. 12 shows a diagrammatic plan of the operation and measuring principle of the urethra sizing tool probes without the transducer. This Figure shows the probes relative positions as inserted in their smallest cross-section size;

FIG. 13 shows as FIG. 12 the same sizing test probes, in a middle distended cross-section size;

FIG. 14 shows as FIG. 12 the same sizing test probes, in their maximum distended cross-section size;

FIG. 15 shows a cross-section of the urethra sizing tool probes and the calculation dimension symbols; and FIG. 16 shows a cross-section through an alternative urethra pressure and sizing test tool probe comprising an inflatable flexible balloon with a transducer attached to its exterior parallel with its longitudinal axis and with both the transducer and the inflatable pressure balloon exterior walls in close pressure contact with the urethra wall interior.

Referring now to FIGS. 1 to 3 of the drawings the preferred embodiment of the urinary control device of the invention is shown in FIG. 1 in situ within the urethra 1 of a male penis 2. The control device shown generally by reference 7 comprises a completely sealed capsule which is air-tight and liquid-proof, the capsule is additionally flexible being made, for example, of silicone rubber or a plastics which may be impregnated with antibiotics on its exterior.

The capsule is solid and as shown in the sectional view of FIG. 2 it has a cross-sectional shape which is generally elliptical providing major and minor cross-sectional axes.

A prestressed metal spring or plastics loop 5 is located in the capsule 7 in such a manner as to apply a predetermined pressure on the major cross-sectional axis of the capsule as shown in FIG. 2. The control device is completed by a withdrawal and anti-migratory loop 11 attached at one end of the body of the capsule to the prestressed spring or loop 5 through a sealed exit in the capsule by a semi-rigid link cord 4.

FIG. 2 shows in section the capsule in situ in the urethra 1 in its maximum stressed shape to prevent involuntary urination.

After manufacture the external major cross-section periphery dimension would be test sized at the specified pressure to be applied for involuntary urine control within the urethra. This data would be recorded and enclosed with each UCD manufactured before enclosing and sealing the device within the sterile safe transit pack before despatch to the customers.

In use, the UCD in situ assumes and maintains its non-voiding urine control shape as shown in FIG. 2. In response, however, to an increase in the physical voiding pressure the capsule is compressed and distorts about its major sectional axis as shown in FIG. 3 to a different reduced cross-sectional area and shape so as to provide a free urine flow area 13 in the urethra between the wall 8 of the urethra and external wall of the capsule. After controlled voiding ceases the reduction in voiding pressure then reduces to the involuntary voiding pressure permitting the device to return to its static, normal involuntary urine control flow shape and position as shown in FIG. 2.

The UCD shown in FIG. 4 is a modified version of the UCD of FIG. 1 in that the capsule comprises a sheath 12 which as before contains the prestressed spring or loop 5 and is furthermore filled with a pressurised gas or liquid 15. The spring or loop 5 at one end extends from the sheath 12 through a sealed exit for the attachment of an external anti-migratory, insertion and removal loop cap 3 by a semi-rigid link 4.

The modified embodiment of the UCD shown in FIGS. 5 and 6 is similar to both FIGS. 1 and 4 in that the capsule body 7 is hollow and the internal cavity 14 is filled with a pressurised gas or liquid 15 or contains a vacuum. FIG. 5 shows the UCD in section in its static condition preventing involuntary urination while FIG. 6 shows the same device in its compressed and distorted condition when subjected to an increased physical voiding pressure.

FIGS. 7 and 8 show an embodiment in which a typical prestressed UCD 19 of the invention is attached to a urethra fixed distending tube 21 in the prostate gland area 22 of the urethra 1. The UCD 19 is attached by a flexible link 20 and is provided at its other end with an external anti-migratory withdrawal loop 3 attached as before by the semi-rigid link 4. FIG. 7 is a vertical section and FIG. 8 shows the arrangement in horizontal section with the UCD in its non-urinating control situation.

FIGS. 9, 10 and 11 show a mechanical urethra sizing and pressure testing tool required to individually size and pressure test every deflated non-urine voiding urethra to which an individual prestressed UCD is to be fitted prior to the selection of an appropriate UCD.

The device has a probe arrangement comprising fixed probe 27 attached to anchor plate 32 which in turn is rigidly fixed to and within the main body handle 36. Also parallel to probe 27 within the probe assembly is an adjustable probe 28 which in turn is rigidly attached to the movable anchor 29 having engraved upon its exterior a sizing scale 30.

Within the anchor 29 is an adjustable screw 31 which when rotated moves the anchor 29 and probe 28 axially and at right angles to the axis of probe 27 by means of the incorporated related meshing threads upon anchor 29 and screw 31.

Enclosing both probes 27 and 28 for sterility is attached a flexible rubber sheath 18 which is retained in position by its reinforced elastic opening being pushed over a suitable location on the anchor plate 32.

The urethra probe in use is inserted within the urethra to a selected depth determined and controlled by the penis location pressure pad 37 on handle 36.

In preparation for insertion of the test probe the rubber sheath 18 is lubricated with an antibacterial gel, and prior to insertion the adjustable movable sizing and pressure screw 31 is rotated anti-clockwise so that the width 33 at right angles to the probe axis is at a minimum, usually 5 mm. See FIG. 12 which shows the penis entrance size formed in such a manner as to reduce expansion of the penis slit entrance to a minimum during the test probe insertion and sizing operation.

When inserted and sizing is taking place the adjustment screw 31 is rotated clockwise in the opposite direction to increase the width at right angles to the probe axis which may be increased to as much as 17 mm. depending upon the patient (see FIG. 13 showing a width 34 of 12 mm. and FIG. 14 showing a width 35 of 15 mm.)

FIG. 15 shows a diagrammatic section through the probe assembly head.

When the probes are nearly fully adjusted within the urethra pressure will be exerted by the urethra upon the external sides of the two probes 27 and 28 FIGS. 10 and 27 and 28 FIG. 15 which will increase as the probe gap 33, 34 and 35 is progressively increased.

This pressure will be indicated by a pressure gauge located at 24 due to the applied tip pressure of the adjustable pressure screw, 31 alternatively a pressure transducer located firmly on a support 38 which in turn is secured to the handle 36 and/or an internal pressure transducer 25 located internally or externally to the flexible probe sheath 18 to read out upon a digital control indicator, via leads 26.

When the urethra wall in contact with sheath 18 applies the desired pressure upon the sides of the two probes 27 and 28 and transducers 24 and 25 adjustment of screw 31 is stopped and the urethra dimension read out upon scale 30 which relates to dimension W on FIG. 15.

The results should be recorded and then the adjustable screw 31 rotated anti-clockwise so as to relax the probe pressure and return same to the minimum width position 33 FIG. 12 to allow easy removal of the probe assembly and pressure tool complete from the urethra.

The permissable and required prestressed pressure within the urethra comprises, the summation of several component pressures as listed below all of which have to be considered.

The peripheral dimension of a section taken through the inserted assembly shown (FIG. 15) is:

$$\{2(W-d)+\pi d\} \text{ mm.}$$

and this will be equal to the required elliptical periphery of the maximum cross section taken through a prestressed and undeformed UCD to be inserted within that particular urethra for the control of involuntary urination at a pressure of $P_{CT}$.

For test purposes the dimension (d) should preferably be as small as possible (e.g. about 1 mm.).

From the known UCD elliptical periphery dimension obtained as shown above a UCD may be selected with an equivalent maximum cross-sectional size and prestressed at the selected and required pressure.

The resultant pressure gauge or transducer digital read-out pressure will comprise the following components:

$$P_{TP} = \{P_{LS} + (P_{CP} + P_E + P_M)\} \text{ OR}$$
$$P_{LS} = (P_{TP} - P_{CT})$$

where
- $P_{TP}$ = Total pressure as shown on the digital read-out.
- $P_E$ = External atmospheric pressure being applied onto the relaxed flattened urethra tube.
- $P_M$ = Muscular residual pressure if any within the non-sphincter controlled urethra test area.
- $P_{LS}$ = Latex sheath stretch pressure and size required during mechanical sizing tests—previously measured with the mechanical device for different urethra widths on scale (30) prior to insertion within the urethra, and check tested for each different sheath being used on the test device.
- $P_{CP}$ = Control pressure—the selected additional pressure to be applied to the urethra interior by the UCD selected to control involuntary urination—dependent upon the patient and his requirements.

UCD Total control pressure within urethra = $P_{CT} = \{P_{CP} + (P_E + P_M)\}$

Note: The combined ($P_E + P_M$) can be directly obtained by insertion of a pressure transducer probe into the urethra area being treated and recording the digital read out prior to the commencement of the sizing test.

The desired pressure in transducer (25) will be $(P_{CT}) = (P_{CP} + P_E + P_M)$ and from the dimension (W) at this point and the preceding formulae the urethra circumference can be calculated directly.

Alternatively or as a check, the desired pressure on transducer or gauge (24) will be $(P_{TP})$ and with the known pressure of transducer (25) of $(P_{CT}) = (P_{CP} + P_E + P_M)$. Value $(P_{LS})$ can be calculated from the preceding formula.

Thus for the control pressure $(P_{CT})$ and using $(P_{LS})$ in conjunction with the precalculated and supplied pressure and size tables the related urethra diameter and circumference dimensions will be given for the equivalent UCD.

These supplied Tables will have printed upon them for various $(P_{LS})$ pressures, the equivalent sheath diameter and hence urethra diameter and circumference, related specifically with the type and size of sizing test sheath being used for the test and its equivalent UCD dimension.

The preferred sizing and pressure test fixture for the urethra is described as follows:

FIG. 16 shows an alternative method (based upon the previous formulae) of measuring the urethra internal diameter (1) at any preselected internal control pressure $(P_{CT})$ which may be effected by inserting into the urethra 1 an inflatable sizing test balloon 39 externally connected to a pressurizing bladder and a transducer digital read-out.

Also at the same time a second transducer 25 is inserted into the urethra between the urethra wall 1 and the adjacent outer wall of the test balloon 39.

For testing the balloon 39 would be inflated until the second transducer 25 reads out the UCD combined pressure of $$(P_{CT}) = \{P_{CP} + (P_E + P_M)\}$$

At this point the first transducer will read-out the pressure within the inflatable test balloon $(P_{TP})$ 39.

From the above data as explained previously $(P_{LS})$ can be easily calculated as for transducers 24 and 25 on the previous test fixture, and the corresponding sheath or urethra diameter and circumference related to the specific test balloon 39 used in the test and the correlated UCD dimension.

In this type of test tool after the test has been done and the pressure $(P_{LS})$ obtained, the test probe is deflated and withdrawn.

The test probe balloon 39 may now externally to the urethra be reinflated to pressure $(P_{LS})$ and its outside diameter can be measured with a micrometer, or inserted into one of a set of supplied ring or gap gauges.

Hence the circumference at $(P_{LS})$ can be calculated and related to the UCD required and its equivalent corresponding major axis cross-sectional periphery at the control pressure $(P_{CT})$.

This test device has the added advantage that the tool supplier does not have to test and supply size and pressure tables for each test probe bladder made.

The $(P_{LS})$ and dimension being always obtained at the time of the test by the urologist, and it is also not dependent upon the ambient test area temperature at the time of the test.

It may well be decided on the early stages of the use of UCD's until sufficient field data is obtained that every six months or as required each patient will be retested as the urethra size may expand slightly either due to the increasing age of the user or the application of the UCD.

All urethras have to be individually sized and pressure tested by the urologist prior to the fitting of a UCD as urethra sizes may vary from 5.5 mm to 10 mm inside diameter when inflated (i.e., urine voiding). This has to be done by the urologist with a specially designed sizing and pressure testing tool and the data obtained recorded and related to the correct size of specified UCD.

For example, the test fixture probe is inserted within the urethra to the control area situ, and is inflated to ascertain the internal diameter of the urethra at the required involuntary urine control pressure, this is then related to the selection of the required UCD.

The forms of designed test tools are hereinafter described with the preferred type specified, also specified is the operating instructions and the data obtained therefrom.

I claim:

1. A urethra insertable urinary control device comprising a flexible completely sealed capsule means with an exterior sheath, said capsule means having a non-spherical cross-section to a longitudinal axis with a major sectional axis and a minor sectional axis, said capsule means being internally stressed by at least one prestressed spring, said spring being located in said capsule means to apply pressure axially along the major sectional axis of the capsule means whereby said capsule means with sheath when inserted in the urethra applies a predetermined calculated pressure along the internal wall of the urethra so as to distort the cross-sectional shape of the urethra by capsule means distortion to prevent involuntary urination, said prestressed spring having an integral and unitary extension means at one end thereof, said extension means projecting from the capsule means and having an integral insertion antimigratory spring and withdrawal device thereon, and said capsule means when subjected to an increase in physical voiding pressure deforming against the action of said spring along one side of its major sectional axis so as to open a free voiding area in the urethra for voluntary urination between the internal wall of the urethra and the external wall of the capsule means.

2. A device as claimed in claim 1, wherein the flexible internally prestressed capsule means is of a broadly elliptical cross-section of a predetermined pressure and size so as to stress the urethra internal wall at a pressure sufficient to eliminate involuntary urination.

3. A device as claimed in claim 2, wherein said control member comprises a solid capsule.

4. A device as claimed in claim 2, wherein the capsule means is in the form of a hollow sheath having a prestressed spring therein, and said sheath being filled with a liquid or gas under pressure.

5. A device according to claim 1, wherein the external surface of the control device is matt, serrated or striated so as to reduce capillary leakage when the capsule means is fitted within the urethra.

* * * * *